United States Patent
Guala

(10) Patent No.: US 9,585,999 B2
(45) Date of Patent: Mar. 7, 2017

(54) FLOW SYSTEM FOR MEDICAL LINES

(71) Applicant: INDUSTRIE BORLA S.P.A., Moncalieri (Turin) (IT)

(72) Inventor: Gianni Guala, Turin (IT)

(73) Assignee: INDUSTRIE BORLA S.P.A., Moncalieri (IT)

( * ) Notice: Subject to any disclaimer, the term of this patent is extended or adjusted under 35 U.S.C. 154(b) by 50 days.

(21) Appl. No.: 14/413,938

(22) PCT Filed: Jun. 11, 2013

(86) PCT No.: PCT/IB2013/054768
§ 371 (c)(1),
(2) Date: Jan. 9, 2015

(87) PCT Pub. No.: WO2014/009823
PCT Pub. Date: Jan. 16, 2014

(65) Prior Publication Data
US 2015/0297817 A1  Oct. 22, 2015

(30) Foreign Application Priority Data

Jul. 9, 2012  (IT) .............................. TO2012A0601

(51) Int. Cl.
*A61M 1/36* (2006.01)
*A61M 39/22* (2006.01)
(Continued)

(52) U.S. Cl.
CPC ............ *A61M 1/367* (2013.01); *A61M 39/10* (2013.01); *A61M 39/22* (2013.01); *A61M 39/26* (2013.01);
(Continued)

(58) Field of Classification Search
CPC ...... A61M 1/367; A61M 39/10; A61M 39/22; A61M 39/26; A61M 2039/1083;
(Continued)

(56) References Cited

U.S. PATENT DOCUMENTS 5,390,898 A     2/1995  Smedley et al.
5,465,938 A  *  11/1995  Werge .................. A61M 39/04
                                                     137/843
(Continued)

FOREIGN PATENT DOCUMENTS

EP    1093828 A2    4/2001
EP    1584346 A1   10/2005
(Continued)

OTHER PUBLICATIONS

International Search Report for PCT/IB2013/054768 dated Sep. 30, 2013.

*Primary Examiner* — Emily Schmidt
*Assistant Examiner* — Lauren M Peng
(74) *Attorney, Agent, or Firm* — Heslin Rothenberg Farley & Mesiti P.C.; Victor A. Cardona, Esq.

(57) ABSTRACT

A flow system for medical lines includes a flow component having a main duct and at least one lateral tubular fitting with a female luer cone communicating with the main duct) through a valve. The valve includes a transverse diaphragm normally kept in fluid-tight contact against an annular valve seat of the lateral tubular fitting, which can be moved away from this into an opening position following upon insertion of a male luer-cone introducer of fluid into the lateral tubular fitting. The diaphragm is prearranged for being pushed into the opening position directly by the introducer, and the lateral tubular fitting is configured to couple in a fluid-tight way with the introducer before the latter comes into contact of thrust with the diaphragm.

6 Claims, 3 Drawing Sheets

(51) Int. Cl.
*A61M 39/10* (2006.01)
*A61M 39/26* (2006.01)
*A61M 39/24* (2006.01)

(52) U.S. Cl.
CPC ............ *A61M 2039/1083* (2013.01); *A61M 2039/246* (2013.01); *A61M 2039/2433* (2013.01); *A61M 2039/261* (2013.01)

(58) Field of Classification Search
CPC .... A61M 2039/2433; A61M 2039/246; A61M 2039/261
See application file for complete search history.

(56) References Cited

U.S. PATENT DOCUMENTS

| | | | |
|---|---|---|---|
| 2004/0068239 A1* | 4/2004 | Utterberg | A61M 39/02 604/256 |
| 2006/0149213 A1 | 7/2006 | Raybuck | |
| 2008/0004600 A1* | 1/2008 | Kitani | A61M 39/10 604/533 |

FOREIGN PATENT DOCUMENTS

| | | |
|---|---|---|
| EP | 1661599 A1 | 5/2006 |
| WO | 0204065 A2 | 1/2002 |

* cited by examiner

FLOW SYSTEM FOR MEDICAL LINES

CROSS REFERENCE TO RELATED APPLICATIONS

This application is a National Stage of PCT International Application No. PCT/IB2013/054768, filed on Jun. 11, 2013, and published in English on Jan. 16, 2014 as WO 2014/009823 A1, which claims priority from Italian Patent Application No. TO 2012 A 000601 filed on Jul. 9, 2012, the entire disclosures of which are incorporated herein by reference.

FIELD OF THE INVENTION

The subject of the present invention is a flow system for medical lines, in particular for haemodialysis, of the type comprising a flow component having a main duct for a primary fluid and at least one lateral tubular fitting with female luer cone communicating with the main duct through a valve.

PRIOR ART

A flow component of the type defined above is known from the European patent No. EP-B-1661599 filed in the name of the present applicant, in which the valve is a so-called anti-siphon valve, including a diaphragm constituted by the bottom wall of a cup-shaped element made of elastically deformable material, the outer peripheral edge of which is normally kept in fluid-tight contact against an annular valve seat of the lateral tubular fitting. As is also described in the patent No. EP-B-1093828, which is also filed in the name of the present applicant, the sealing edge of this valve can be moved away from the corresponding annular valve seat, to an opening position, following upon insertion of a male luer-cone introducer of fluid within the female luer cone of the lateral tubular fitting. It is hence a two-way valve of the so-called "luer activated" type, opening of which is controlled mechanically, rather than simply by the pressure of the fluid introduced into the lateral tubular fitting.

Mechanical activation is normally obtained in the case of valves of this sort, with the aid of additional components. For example, from the Italian patent No. IT-B-1291508, which is also filed in the name of the present applicant, opening of a diaphragm valve obtained as a result of insertion of the male luer-cone introducer of fluid within a female luer-cone fitting is obtained with the aid of an auxiliary tubular slider that is axially mobile within the fitting and rests against the diaphragm of the valve. Opening of the valve is thus obtained as a result of the axial thrust applied on the diaphragm by the auxiliary slider, which is in turn moved by the male luer-cone introducer.

A similar solution is described in the document No. U.S. Pat. No. 5,565,938A.

This arrangement, in addition to being relatively complicated, may entail the risk of the valve being opened by the auxiliary slider before the male luer-cone introducer provides the hermetic seal with the female luer cone of the tubular fitting, with consequent problems of contamination and leakage of fluid.

SUMMARY OF THE INVENTION

The object of the present invention is to overcome the above drawback and to provide a flow system for medical lines of the type defined in the pre-characterizing part of claim 1 (and generally corresponding to what is described and illustrated in the already cited European patent No. EP-B-1661599), in which opening of the valve upon insertion of the introducer of fluid takes place in a precise and reliable way and without any risk of contamination.

According to the invention, this object is achieved thanks to the fact that the diaphragm of the valve is prearranged for being pushed towards the aforesaid opening position as a result of the direct contact of thrust by the male luer-cone introducer of fluid and to the fact that the lateral tubular fitting is configured in such a way as to couple in a fluid-tight way with the aforesaid introducer before the latter comes into contact of thrust with the aforesaid diaphragm.

According to a preferred embodiment of the invention, the lateral tubular fitting is made of a relatively gelding elastic material and is conveniently elastically expandable in a radial direction following upon fluid-tight coupling of the aforesaid introducer of fluid to the female luer cone of the lateral tubular fitting.

The radial expansion of the lateral tubular fitting may be conveniently obtained envisaging that its side wall is locally thinned axially.

BRIEF DESCRIPTION OF THE DRAWINGS

The invention will now be described in detail with reference to the annexed drawings, which are provided purely by way of non-limiting example and in which.

DETAILED DESCRIPTION OF THE INVENTION

Figure 1:
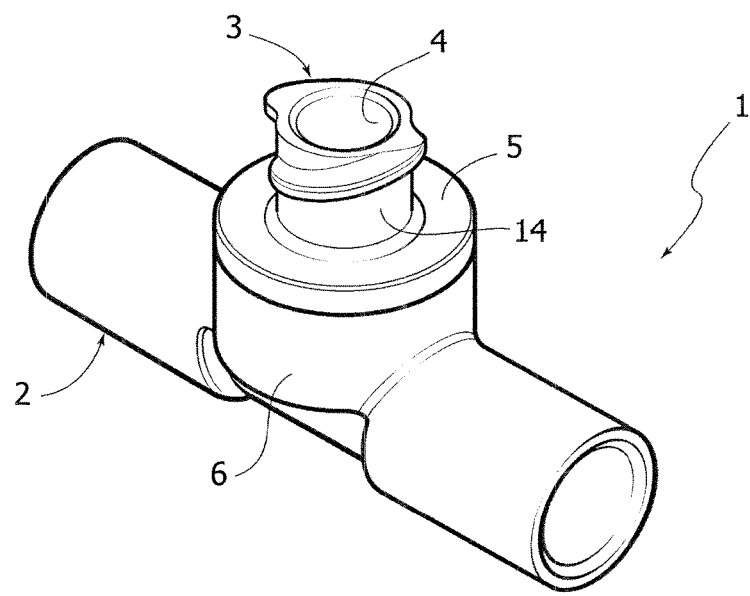
FIG. 1 is a schematic perspective view of a flow system for medical lines according to the invention.
Figure 2:
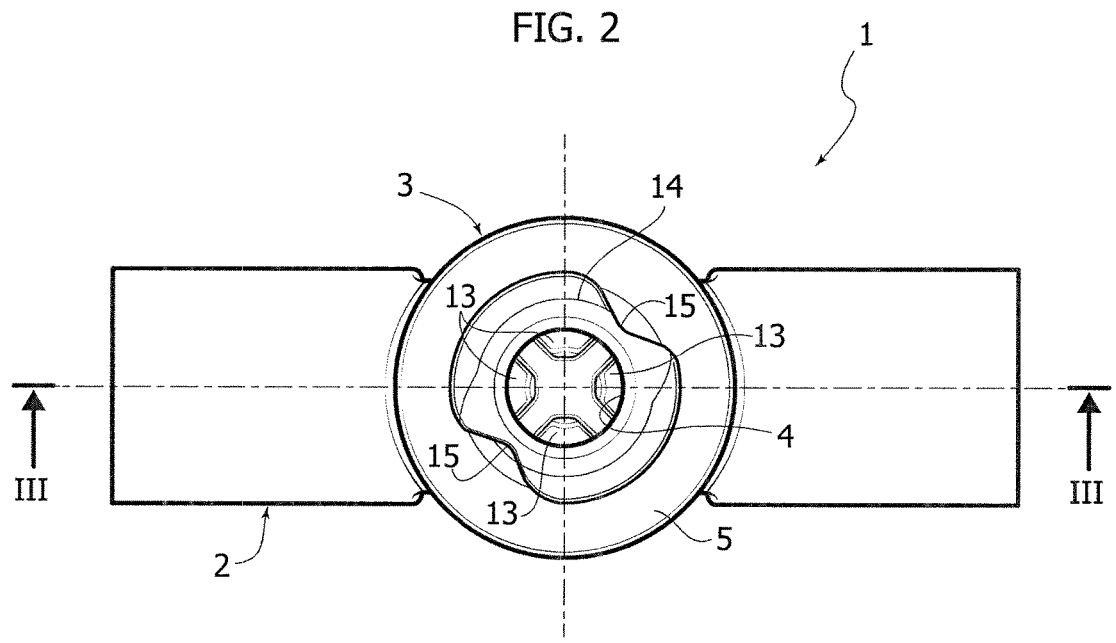
FIG. 2 is a top plan view at a larger scale of the system of FIG. 1.

The flow system according to the invention represented in the drawings may be applied in particular to a medical haemodialysis line.

The flow system basically comprises a flow component 1 having a main duct 2 designed in use to be traversed by the flow of a primary fluid in the direction indicated by the arrow A, and a lateral tubular fitting 3 extending in a direction perpendicular to the duct 2 for introduction of a secondary fluid into the latter.

The lateral tubular fitting 3 is shaped like a female luer-lock connector, the luer-cone internal surface of which is designated by 4, and the internal end of which has an annular flange 5 fixed in a fluid-tight way at an annular collar 6 projecting laterally from the main duct 2.

Figure 5:
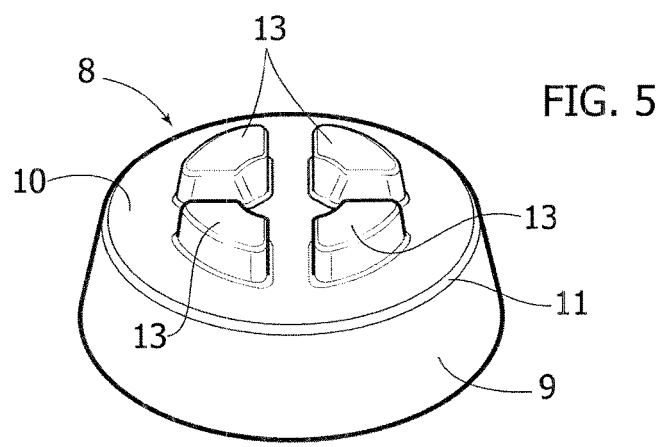
FIG. 5 is a perspective view of the open/close element of the anti-siphon valve of the flow component.
Figure 6:
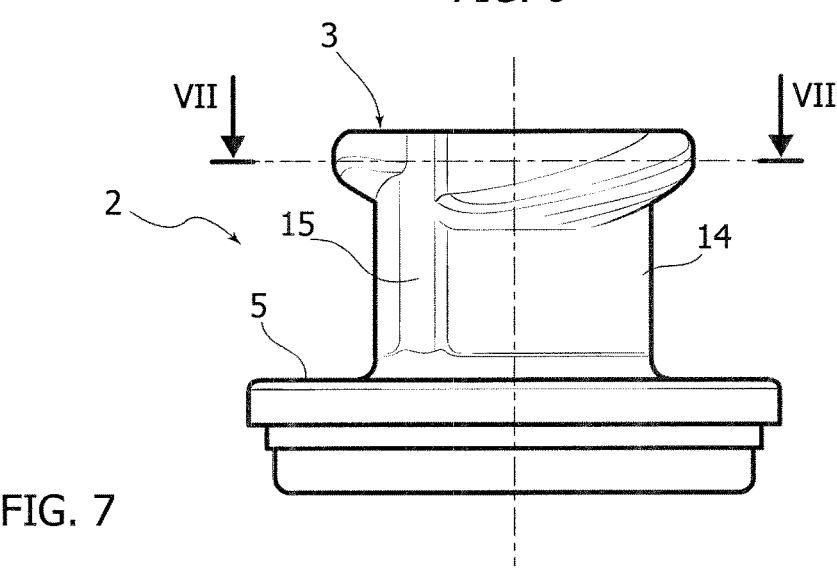
FIG. 6 is a view in elevation of the lateral tubular fitting of the flow component.

Defined between the annular flange 5 and the annular collar 6 is a chamber 7 for a two-way valve, the general conformation of which is known from the already cited European patents Nos. EP-B-1093828 and EP-B-1661599. In detail, and as is more clearly visible also in FIG. 5, the valve comprises an element 8 shaped like a cup turned upside down made of elastic material, for example, silicone, the side wall 9 of which rests on the bottom of the chamber 7 and the bottom wall of which, designated by 10, defines an elastically deformable transverse diaphragm, the perimetral edge 11 of which is normally set in hermetic contact against an annular valve seat 12 with conical surface formed inside the annular flange 5 of the lateral tubular fitting 3. The hermetic contact is obtained thanks to the axial thrust applied by the side wall 9 of the cup-shaped element 8 on the diaphragm 10.

The diaphragm 10 is formed with a ring of axial projections 13 (in the example illustrated, four in number), which radially face the base of the female luer cone 4 of the lateral tubular fitting 3 and the function of which will be clarified in what follows.

Figure 7:
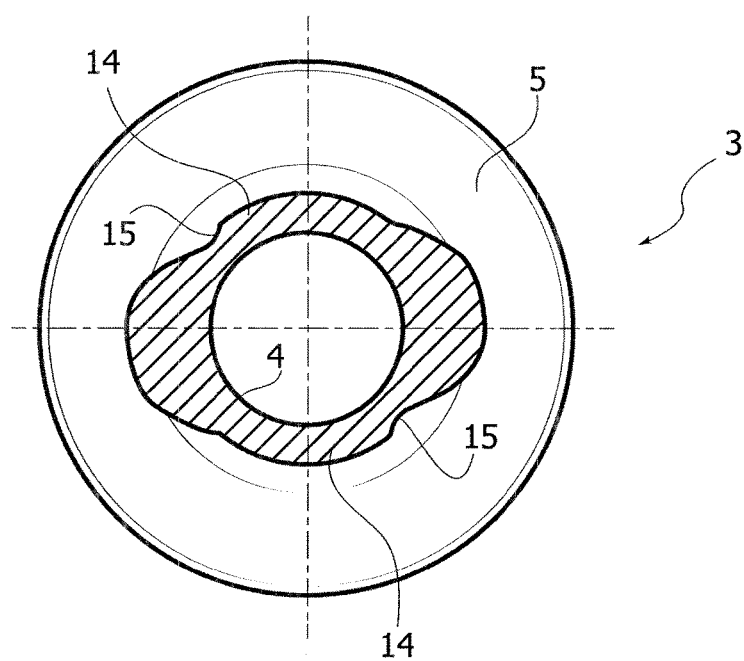
FIG. 7 is a view in axial section according to the line VII-VII of FIG. 6.

The lateral tubular fitting 3 advantageously has two peculiar characteristics: in the first place, it is made of a relatively gelding i.e. compliant elastic material (for example, polybutylene-terephthalate and analogues), and preferably its side wall is locally thinned axially, for example, in the way represented in FIG. 7, with two diametrally opposite portions 14 thinner than the remaining portions 15, which are thicker.

Figure 3:
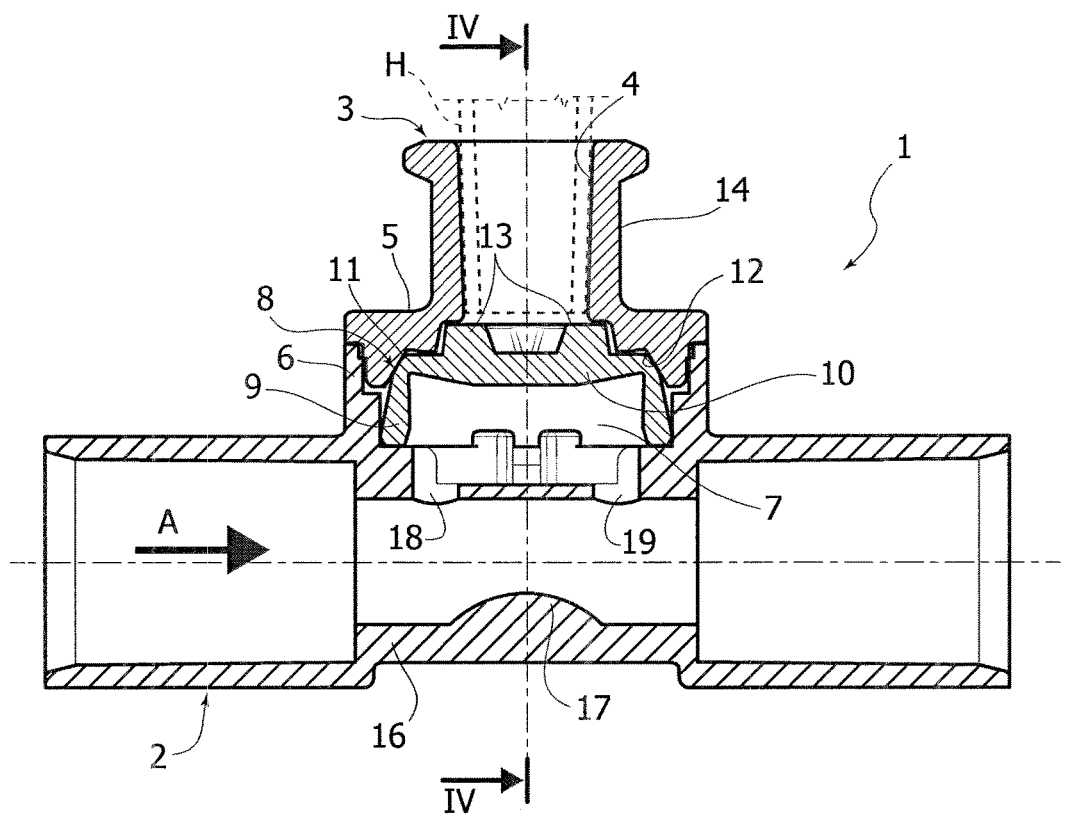
FIG. 3 is a longitudinal sectional view according to the line III-III of FIG. 2.
Figure 4:
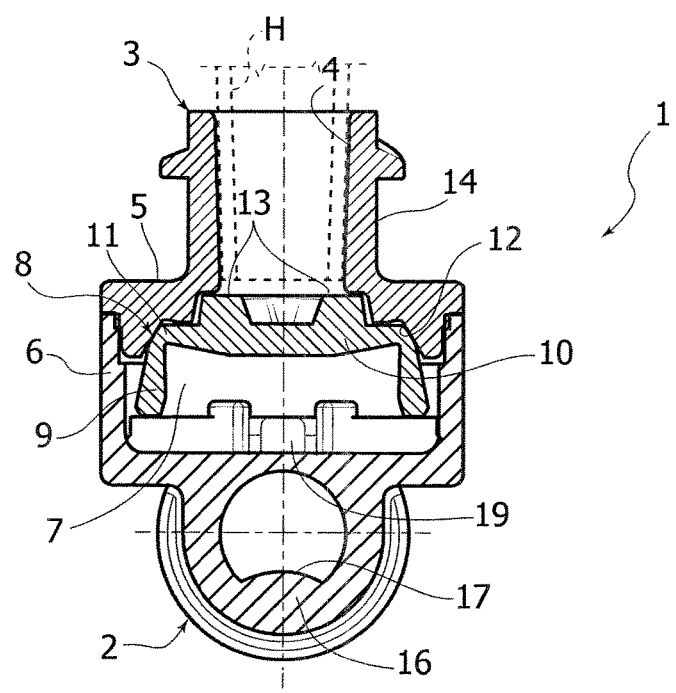
FIG. 4 is a sectional view according to the line IV-IV of FIG. 3.

In the second place, the female luer-cone internal surface 4 is obtained with the minimum tolerance possible in proportion to the size of a normal male luer-cone introducer of fluid, partially represented schematically with a dashed line and designated by H in FIGS. 3 and 4.

These characteristics contribute to achieving the functional effect that will be discussed in what follows.

In the case of the example illustrated, the main duct 2 has, in a region axially corresponding to the chamber 8, a portion 16 with an internal wall having a convergent-divergent profile. This profile is defined by a localized narrowing of rounded shape 17 of the internal wall of the portion 16, upstream of which (with respect to the direction of flow A of the primary fluid) the convergent part is defined, in communication with the chamber 7 through a first radial passage 18, and downstream of which the divergent part is defined, in turn in communication with the chamber 7 through a second radial passage 19. This conformation, which however is not strictly necessary in relation to operation of the valve, corresponds to the one described and illustrated in the already cited patent No. EP-B-1661599, with the functional effect that will also be described in what follows.

In operation, as explained previously, the valve defined by the cup-shaped element 8 is normally set in the closing position, with the peripheral edge 11 of the diaphragm 10 kept in fluid-tight contact against the annular valve seat 12 as a result of the axial thrust exerted by the side wall 9.

For introduction of a secondary fluid within the main duct 2 (or else for extraction of fluid from the main duct 2), the male luer-cone introducer H is introduced axially into the lateral tubular fitting 4 and pushed therein. Considering the minimal tolerance referred to above, the hermetic seal between the male luer cone of the introducer H and the female luer cone 4 of the lateral tubular fitting 3 is obtained already at a certain distance from the axial projections 13 of the diaphragm 10, i.e., approximately in the area represented in FIGS. 3 and 4. The further axial advance of the introducer H, made possible by the radially gelding and possibly locally thinned conformation of the lateral tubular fitting 3 referred to above, produces interaction thereof with the axial projections 13 of the diaphragm 10 and separation of the perimetral edge 11 of the latter from the valve seat 12, against the action of thrust applied by the side wall 9. In this way, there is allowed flow of the secondary fluid from the introducer H to the chamber 7 and thus into the main duct 2, or vice versa. In this step, the cross section with a convergent-divergent profile 16 defines a Venturi tube designed to prevent the stagnation of the secondary fluid within the chamber 7. Part of the flow of the primary liquid penetrates into the chamber 7 through the first passage 18 and comes out of this through the second passage 19, entrained thanks to the ejecting effect obtained by the aforesaid flow of the primary fluid in the area of the divergent profile. In this way, the primary fluid in the main duct 2 achieves not only an effect of emptying of the chamber 7, but also an effective action of continuous flushing thereof.

When the introducer H is taken out of the lateral tubular fitting 3, the latter is brought back again into its undeformed condition, and the side wall 9 of the cup-shaped element 8 brings the diaphragm 10 back into the closing position, pushing the perimetral edge 11 again into fluid-tight contact with the annular valve seat 12.

Of course, the details of construction and the embodiments may vary widely with respect to what has been described and illustrated herein, without thereby departing from the scope of the present invention as defined in the ensuing claims.

The invention claimed is:

1. A flow system for medical lines comprising:
    a flow component having a main duct for a primary fluid and at least one lateral tubular fitting with a female luer cone communicating with the main duct through a valve;
    said valve comprising a transverse diaphragm formed by a bottom wall of a cup-shaped element made of elastically deformable material, and a male luer-cone introducer of secondary fluid:
    said cup-shaped element having an outer peripheral edge normally kept in fluid-tight contact against an annular valve seat of said at least one lateral tubular fitting:
    said male luer-cone introducer of secondary fluid, insertable into said at least one lateral tubular fitting with female luer cone to displace said transverse diaphragm into an opening position;
    said diaphragm prearranged for being pushed into said opening position as a result of a direct contact of thrust by said introducer, said lateral tubular fitting configured to couple in a fluid-tight way with said introducer before said introducer comes into the contact of thrust with said diaphragm;
    said lateral tubular fitting formed of a relatively yielding elastic material and expandable elastically in a radial direction following upon fluid-tight coupling with said introducer;
    a side wall of said lateral tubular fitting having two diametrically opposite axial portions which are thinner than remaining portions of said sidewall; and
    wherein said diaphragm is formed with a ring of axial projections radially facing a base of said female luer cone such that a contact of said introducer with said ring of axial projections allows a flow from the introducer into said main duct.

2. The flow system according to claim 1, wherein said lateral tubular fitting has a wall locally thinned axially.

3. The flow system according to claim 1 wherein said diaphragm has a ring of axial projections radially facing said female luer cone.

4. The flow system according to claim 3, wherein the outer peripheral edge of said diaphragm is normally kept in fluid-tight contact against said annular valve seat under the action of an axial thrust applied by a side wall of said cup-shaped element, the deflection of said diaphragm produced in use following upon the interaction between said introducer and said axial projections bringing about radial contraction of said peripheral edge and its consequent separation from said annular valve seat.

5. The flow system according to claim 1 wherein said main duct has, in a position corresponding to said valve, an axial section with a convergent-divergent profile.

6. The flow system according to claim 1 wherein said contact of said introducer with said ring of axial projections causes said outer peripheral edge to separates from, and not be in fluid-tight contact with, said annular valve seat.

* * * * *